US006988826B2

(12) United States Patent
Zribi et al.

(10) Patent No.: US 6,988,826 B2
(45) Date of Patent: Jan. 24, 2006

(54) NANO-CALORIMETER DEVICE AND ASSOCIATED METHODS OF FABRICATION AND USE

(75) Inventors: Anis Zribi, Rexford, NY (US); Azar Alizadeh, Wilton, NY (US); Suryaprakash Ganti, Clifton Park, NY (US); Juan Antonio Sabate, Gansevoort, NY (US); Loucas Tsakalakos, Niskayuna, NY (US); Kenneth Roger Conway, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/847,180

(22) Filed: May 17, 2004

(65) Prior Publication Data

US 2005/0254547 A1    Nov. 17, 2005

(51) Int. Cl.
*G01K 17/00*    (2006.01)
*G01N 25/00*    (2006.01)

(52) U.S. Cl. .............................. 374/31; 374/10; 374/29; 436/147; 422/51

(58) Field of Classification Search .................. 374/29, 374/30, 31, 10, 11, 208; 73/25.03; 438/48, 438/54; 436/147; 422/51
See application file for complete search history.

(56) References Cited

U.S. PATENT DOCUMENTS

| | | | | |
|---|---|---|---|---|
| 3,899,918 A | * | 8/1975 | Privalov et al. | ............... 374/11 |
| 4,492,480 A | * | 1/1985 | Wadso et al. | .................. 374/33 |
| 4,902,138 A | * | 2/1990 | Goeldner et al. | ............. 374/44 |
| 5,779,363 A | * | 7/1998 | Freire et al. | ................... 374/33 |
| 5,801,070 A | * | 9/1998 | Zanini-Fisher et al. | ....... 438/54 |
| 5,813,764 A | * | 9/1998 | Visser et al. | ................... 374/12 |
| 5,967,659 A | * | 10/1999 | Plotnikov et al. | ............. 374/11 |
| 6,079,873 A | * | 6/2000 | Cavicchi et al. | .............. 374/10 |
| 6,193,413 B1 | * | 2/2001 | Lieberman | .................... 374/45 |
| 6,238,085 B1 | * | 5/2001 | Higashi et al. | ................ 374/10 |
| 6,290,388 B1 | * | 9/2001 | Saul et al. | ..................... 374/44 |
| 6,331,074 B1 | * | 12/2001 | Kimura | ........................ 374/10 |

(Continued)

FOREIGN PATENT DOCUMENTS

JP          11094655 A    *   4/1999

OTHER PUBLICATIONS

Calorimetry Science Corp. Calorimeter, Microcalorimeter and nanocalorimeter. Ad Broshure. Internet. No date.*

(Continued)

*Primary Examiner*—Gail Verbitsky
(74) *Attorney, Agent, or Firm*—Paul J. DiConza; William E. Powell, III

(57) ABSTRACT

The present invention provides a nano-calorimeter device operable for measuring and characterizing the thermodynamic and other physical properties of materials that are confined to essentially nano-scale dimensions. The nano-calorimeter device including a thin film membrane having a first surface and a second surface. The nano-calorimeter device also including a frame structure disposed adjacent to and in thermal contact with the first surface of the thin film membrane, the frame structure defining a plurality of hollow cells adjacent to and in thermal contact with the first surface of the thin film membrane. The nano-calorimeter device further including one or more micro-heating elements disposed adjacent to and in thermal contact with the second surface of the thin film membrane, the location of the one or more micro-heating elements disposed adjacent to the second surface of the thin film membrane substantially corresponding to the location of the plurality of hollow cells defined adjacent to the first surface of the thin film membrane.

35 Claims, 11 Drawing Sheets

U.S. PATENT DOCUMENTS

| | | | |
|---|---|---|---|
| 6,402,369 B1 * | 6/2002 | Ludington et al. | 374/13 |
| 6,439,765 B2 * | 8/2002 | Smith | 374/31 |
| 6,460,411 B1 * | 10/2002 | Kersjes et al. | 73/204.26 |
| 6,596,236 B2 * | 7/2003 | DiMeo, Jr. et al. | 422/88 |
| 6,786,632 B2 * | 9/2004 | Tanaka et al. | 374/31 |
| 6,843,596 B2 * | 1/2005 | Verhaegen | 374/10 |
| 2002/0150683 A1 * | 10/2002 | Troian et al. | 427/256 |
| 2003/0043879 A1 * | 3/2003 | Tanaka et al. | 374/31 |
| 2003/0186453 A1 * | 10/2003 | Bell et al. | 436/147 |
| 2004/0023302 A1 * | 2/2004 | Archibald et al. | 435/7.1 |
| 2004/0115711 A1 * | 6/2004 | Su et al. | 435/6 |

OTHER PUBLICATIONS

A Suspended Membrane Nanocalorimeter for Ultralow Volume Bioanalysis. Erik Johannesse et al. IEEE, vol. 1, No.1, Mar. 2002.*

Efremov et al., "Discrete Periodic Melting Point Observations for Nanostructure Ensembles," Physical Review Letters, vol. 85, No. 17, pp. 3560-3563 (Oct. 23, 2000).

Kwan et al., "Nanoscale Calorimetry of Isolated Polyethylene Single Crystals," Journal of Polymer Science: Part B: Polymer Physics, vol. 39, pp. 1237-1245 (2001).

Olson et al., "The Design and Operation of a MEMS Differential Scanning Nanocalorimeter . . . ," Journal of Microelectromechanical Systems, vol. 12, No. 3, pp. 355-364 (Jun. 2003).

Efremov et al., "Thin-Film Differential Scanning Calorimetry: A New Probe for Assignment of the Glass . . . ," Macromolecules, vol. 35, No. 5, pp. 1481-1483 (Feb. 26, 2002).

* cited by examiner

NANO-CALORIMETER DEVICE AND ASSOCIATED METHODS OF FABRICATION AND USE

FIELD OF THE INVENTION

The present invention relates generally to the fields of nano-technology and differential scanning calorimetry. More specifically, the present invention relates to a near-adiabatic nano-calorimeter device and associated methods of fabrication and use. The nano-calorimeter device of the present invention is used to measure and characterize the thermodynamic and other physical properties of materials that are confined to essentially nano-scale dimensions.

BACKGROUND OF THE INVENTION

The thermodynamic and other physical properties of materials that are confined to essentially nano-scale dimensions, such as organic (polymeric and biological) and inorganic ultra-thin (essentially two-dimensional or surface) films and nano-particles, differ significantly from those of bulk (essentially three-dimensional) materials. For example, organic ultra-thin films and nano-particles typically have heat capacities that are relatively smaller and demonstrate thermal transitions and changes over relatively broader ranges, with relatively shallow thermal transitions and changes. This makes the measurement and characterization of heat capacities, thermal transitions (such as melting points, glass transition temperatures, and the like), and thermal changes associated with the formation of new products (such as heats of reaction in single and multi-layer samples and the like) more difficult. In addition, the heats involved are typically on the order of about 1 nJ or less. Thus, conventional devices and methods used to measure and characterize the thermodynamic and other physical properties of bulk materials, such as conventional differential scanning calorimeters and the like, are inadequate for the measurement and characterization of the thermodynamic and other physical properties of ultra-thin films and nano-particles due to their lack of sensitivity, and because such devices and methods are not used at near-adiabatic conditions. In general, these devices and methods incorporate relatively large thermal mass addenda and time constants.

A number of nano-calorimeter devices have been developed and fabricated to measure and characterize the thermodynamic and other physical properties of ultra-thin films and nano-particles. However, most of these nano-calorimeter devices suffer from undesirable thermal leaks. Most of the conventional nano-calorimeter devices incorporate a plurality of micro-mechanical sensors, polymeric membranes, or thin film silicon nitride ($SiN_x$) membranes on which one or more samples are deposited. Experiments are performed under vacuum conditions in order to minimize thermal leakage by convection and ultra-fast heat pulses are used in order to make thermal leakage by conduction negligible in comparison with the heating rates.

For example, Efremov et al. ("Discrete Periodic Melting Point Observations for Nanostructure Ensembles," Physical Review Letters, Vol. 85, No. 17, pp. 3560–3563 (Oct. 22, 2000)) disclose a nano-calorimeter device that includes a thin film (30 nm) silicon nitride ($SiN_x$) membrane that is several millimeters wide. Two metallic strips consisting of Ni, Au, or Pt, each with a thickness of 50 nm and a width of 400 $\mu$m, are deposited on one side of the silicon nitride membrane and serve as both micro-heaters and resistive thermometers. By using a thin silicon nitride membrane as the support system, the sensor has relatively low thermal mass addenda. The variation of the resistance of the micro-heaters with temperature is calibrated prior to use. Relatively fast heating rates (up to $10^6$ K/s) are used, minimizing conductive and radiative heat losses. Thus, the nano-calorimeter device, including the metallic strips, a sample ultra-thin film deposited directly on the surface of the silicon nitride membrane and adjacent to one of the metallic strips, and a portion of the silicon nitride membrane itself, is operated at near-adiabatic conditions. Calorimetric measurements are performed in a differential scanning mode, with one of the metallic strips serving as a reference sensor. Calorimetric measurements proceed by applying a current pulse to both of the metallic strips, sample and reference, simultaneously. The voltage and current across the micro-heaters are measured and used to calculate power, temperature, and heat capacity in, for example, a study of melting points.

Kwan et al. ("Nanoscale Calorimetry of Isolated Polyethylene Single Crystals," Journal of Polymer Science: Part B: Polymer Physics, Vol. 39, pp. 1237–1245 (2001)) disclose a nano-calorimeter device that includes a thin film (30 nm) amorphous silicon nitride ($a-Si_3N_{4-x}$) membrane supported by a silicon frame. A thin (50 nm) patterned Pt strip (500 $\mu$m×5 mm, ~70 $\Omega$) is deposited on one side of the silicon nitride membrane and used as both a micro-heater and a resistive thermometer. The material of interest is deposited on the silicon nitride-side of the silicon nitride membrane, adjacent to the micro-heater/thermometer. Differential scanning calorimetry is performed after calibration using two identical sensors in a common setup: a sample sensor (with the material of interest) and a reference sensor (without the material of interest). The calorimetric measurement of, for example, melting points is initiated with the application of a synchronized direct-current (DC) electrical pulse (9–25 mA, 2–10 ms) to each micro-heater. High heating rates ($2\times10^4$–$2\times10^5$ degrees C./s) under high-vacuum conditions ($\sim10^{-6}$ Torr) allow the measurements to approach adiabatic conditions.

While existing nano-calorimeter devices allow for higher sensitivities and shorter response times than conventional differential scanning calorimeters in measuring phase transition temperatures and heat capacity changes, these nano-calorimeter devices have not been designed and optimized to obtain highly-accurate quantitative calorimetric measurements. For example, in designs proposed and used by Allen et al. ("The Design and Operation of a MEMS Differential Scanning Nanocalorimeter for High-Speed Heat Capacity Measurements of Ultrathin Films," Journal of Microelectromechanical Systems, Vol. 12, No. 3, pp. 355–364, (June, 2003) and "Thin-Film Differential Scanning Calorimetry: A New Probe for Assignment of the Glass Transition of Ultrathin Polymer Films," Macromolecules, Vol. 35, No. 5, pp. 1481–1483 (Feb. 26, 2002)), the sample and reference cells are either not physically connected or exist in close proximity to one another with no heat sink provided between them. Thus, what is needed is a nano-calorimeter device that allows for differential scanning measurements wherein, in a symmetrical configuration, inherent measurement errors due to thermal leakage are equal in both cells and easily counterbalanced. What are also needed are improved cell and micro-heater designs.

In fact, in each of the references described above, multiple approximations are made regarding the device and the sample in order to extract the heat capacity, introducing errors on the order of magnitude of the measurables. Examples of such approximations include: neglecting convective, conductive, and radiative thermal leakage under pulsing conditions; ignoring cross-talk between the micro-heaters; ignoring thermal lag for certain samples; assuming that interfacial stress effects are insignificant; etc. These approximations considerably simplify the design of the device at the expense of accuracy, sensitivity, resolution, and measurement repeatability. The number of approximations required may be considerably reduced by optimizing the design of the cells, sample, micro-heaters, and thermal shields used.

Thus, in general, what is still needed is an improved nano-calorimeter device that is simple, effective, and further minimizes thermal leakage due to convection, conduction, and radiation, allowing the nano-calorimeter device to operate at near-adiabatic conditions. The nano-calorimeter device should have increased sensitivity and decreased thermal mass. The nano-calorimeter device should also incorporate and utilize power compensation, eliminating the drift that is present in existing nano-calorimeter designs and allowing a more flexible material system to be used.

BRIEF SUMMARY OF THE INVENTION

The present invention provides a near-adiabatic nano-calorimeter device and associated methods of fabrication and use that allow for the measurement and characterization of the thermodynamic and other physical properties of materials that are confined to essentially nano-scale dimensions, such as organic (polymeric and biological) and inorganic ultra-thin (essentially two-dimensional or surface) films and nano-particles. The nano-calorimeter device of the present invention includes one or more twin-cell differential sensors that each incorporate a membrane that has a relatively low heat capacity and thermal conductivity, such as a free-standing thin film silicon nitride ($SiN_x$) membrane, a polymeric membrane, or the like. The silicon nitride or polymeric membrane is supported by a silicon or composite polymeric frame that acts as a heat sink to cool a sample that is deposited on the surface of the silicon nitride or polymeric membrane and achieve adequate temperature control. In the case that a polymeric membrane and a composite polymeric frame are used, thermally-conductive nano-particles (such as Au, Ag, or Fe nano-particles) are dispersed in a relatively thick (up to about 600 $\mu$m) polymeric film to form the composite polymeric frame and enhance its thermal conductivity. The polymeric membrane is spin coated onto the silicon or composite polymeric frame. The twin-cell differential sensor of the present invention also incorporates a plurality of micro-heating elements, such as a plurality of resistive thin Pt films or the like, and circuitry that is used to control the plurality of micro-heating elements. The present invention also provides an exemplary hot stage that is used to determine the temperature-resistance characteristic of each of the plurality of micro-heating elements and calibrate the nano-calorimeter device. Advantageously, the nano-calorimeter device of the present invention demonstrates reduced thermal leakage due to convection, conduction, and radiation and operates at near-adiabatic conditions.

The present invention also incorporates and utilizes power compensation across the plurality of micro-heating elements. This provides highly accurate heat capacity measurements which, in turn, enable the thermal characterization of ultra-thin films, including monolayers of polymeric films. In a power-compensated twin-cell nano-calorimeter device, the current in the "sample nano-calorimeter" is controlled to match the temperature of the sample with that of the reference using a closed-loop control strategy. The design of the present invention is capable of the high-frequency data manipulation required for temperature control at the extremely fast heating rates that are typically employed in such nano-calorimeter devices.

In one embodiment of the present invention, a nano-calorimeter device operable for measuring and characterizing the thermodynamic and other physical properties of materials that are confined to essentially nano-scale dimensions includes a thin film membrane having a first surface and a second surface. The nano-calorimeter device also includes a frame structure disposed adjacent to and in thermal contact with the first surface of the thin film membrane, the frame structure defining a plurality of hollow cells adjacent to and in thermal contact with the first surface of the thin film membrane. The nano-calorimeter device further includes one or more micro-heating elements disposed adjacent to and in thermal contact with the second surface of the thin film membrane, the location of the one or more micro-heating elements disposed adjacent to the second surface of the thin film membrane substantially corresponding to the location of the plurality of hollow cells defined adjacent to the first surface of the thin film membrane.

In another embodiment of the present invention, a method for fabricating and using a nano-calorimeter device operable for measuring and characterizing the thermodynamic and other physical properties of materials that are confined to essentially nano-scale dimensions includes providing a thin film membrane having a first surface and a second surface. The method also includes disposing a frame structure adjacent to and in thermal contact with the first surface of the thin film membrane, the frame structure defining a plurality of hollow cells adjacent to and in thermal contact with the first surface of the thin film membrane. The method further includes disposing one or more micro-heating elements adjacent to and in thermal contact with the second surface of the thin film membrane, the location of the one or more micro-heating elements disposed adjacent to the second surface of the thin film membrane substantially corresponding to the location of the plurality of hollow cells defined adjacent to the first surface of the thin film membrane.

BRIEF DESCRIPTION OF THE DRAWINGS

Preferred embodiments of the present invention are described in detail herein below, with reference to the accompanying drawings, in which.

DETAILED DESCRIPTION OF THE INVENTION

Figure 1:
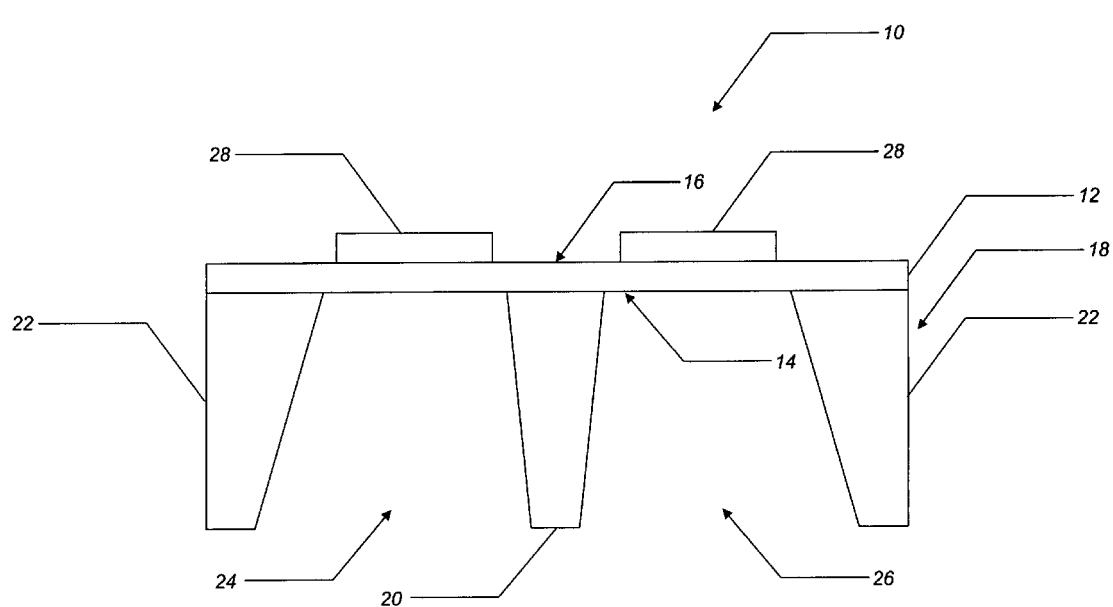
FIG. 1 is a cross-sectional side view of one embodiment of a twin-cell differential sensor associated with the nano-calorimeter device of the present invention.
Figure 8:
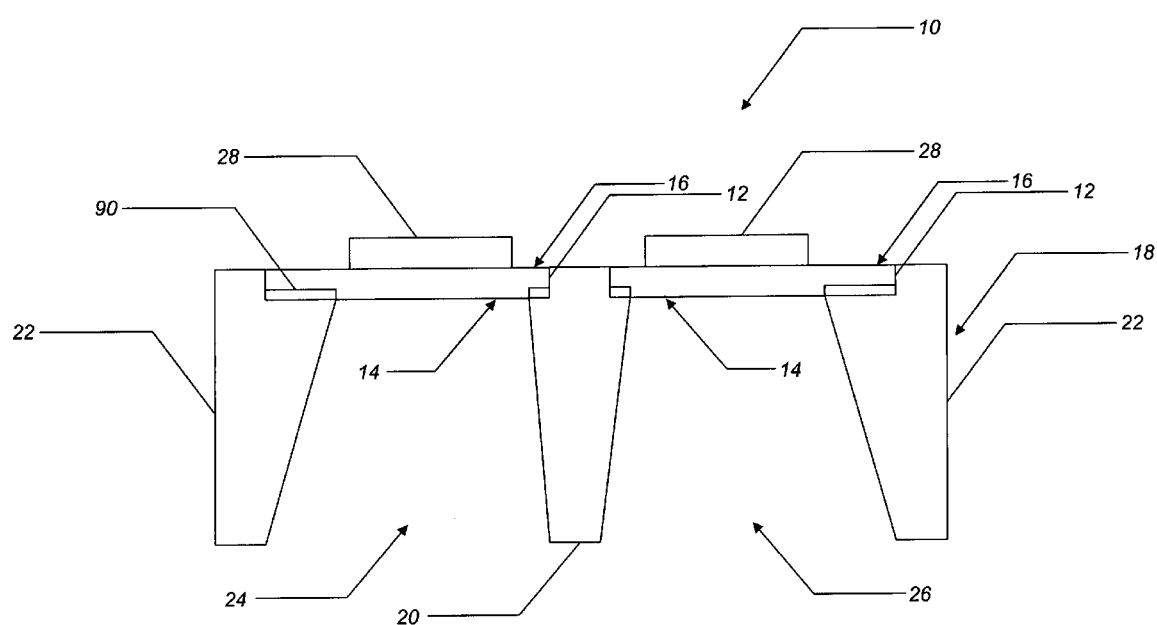
FIG. 8 is a cross-sectional side view of another embodiment of a twin-cell differential sensor associated with the nano-calorimeter device of the present invention, highlighting the use of dielectric isolation.

Referring to FIG. 1, in one embodiment, the nano-calorimeter device of the present invention includes one or more twin-cell differential sensors 10, each of the twin-cell differential sensors 10 comprising a chip transducer that is operable for measuring heat flow. Each of the twin-cell differential sensors 10 includes a membrane 12 that has a relatively low heat capacity and thermal conductivity, such as a free-standing thin film silicon nitride ($SiN_x$) membrane, a polymeric membrane, or the like. $Si_3N_x$ or the like may also be used. The membrane 12 has a first surface 14 and a second surface 16, and a thickness of between about 20 nm and about 5000 nm, preferably between about 30 nm and about 100 nm. The membrane 12 has a width of between about 100 nm and about 10 mm, preferably about 2 mm, and a length of between about 100 nm and about 10 mm, preferably about 5 mm. Optionally, a thermally-insulating dielectric layer 90 (FIG. 8) ($SiO_2$, air, etc.) is disposed adjacent to and in thermal contact with all or a portion of the first surface 14 of the membrane 12 (see FIG. 8). A frame 18 is disposed adjacent to and in thermal contact with the first surface 14 of the membrane 12. Optionally, the thermally-insulating dielectric layer 90 (FIG. 8) is disposed between the frame 18 and the membrane 12 (see FIG. 8). The frame 18 is made of Si, SiC, a composite polymeric material, a composite polymeric material containing dispersed metallic nano-particles, or any other suitable material having a relatively high thermal conductivity. The frame 18 has a thickness of between about 50 μm and about 600 μm. The frame 18 has a width of between about 100 μm and about 30 mm, preferably about 13 mm, and a length of between about 100 μm and about 30 mm, preferably about 13 mm. The frame 18 includes a center member 20 and a plurality of side members 22 that collectively divide the first surface 14 of the membrane 12, and the space disposed adjacent thereto, into a first cell 24 and a second cell 26. A sample (not shown) is selectively disposed adjacent to and in thermal contact with the first surface 14 of the membrane 12 within the first cell 24 and/or the second cell 26 defined by the frame 18, forming a sample sensor and a reference sensor.

Preferably, the sample includes an organic (polymeric or biological) or inorganic ultra-thin (essentially two-dimensional or surface) film or nano-particle, or one or more nano-rods. In general, the sample is confined to essentially nano-scale dimensions, with a thickness of between about 1 pm and about 10 microns and a total sample mass of between about 1 ng and about 1000 μg. Exemplary samples include, but are not limited to, polymeric materials, ceramic materials, metallic materials, composite materials, and bio-materials, and may exist in any of the solid, liquid, or adsorbed gaseous states. The sample is deposited on the first surface 14 of the membrane 12 using, for example, a spin coating technique, a chemical vapor deposition (CVD) technique, an evaporation technique, a liquid dispensing technique, a soft-stamp transfer technique, or any other suitable sample transfer technique. The sample may also be grown in-situ on the first surface 14 of the membrane 12. In an alternative embodiment, the sample is selectively disposed adjacent to and in thermal contact with the second surface 16 of the membrane 12. Advantageously, the frame 18 supports the membrane 12 and acts as a heat sink to cool the sample that is deposited on the first surface 14 or second surface 16 of the membrane 12 and achieve adequate temperature control.

A plurality of micro-heating elements 28 are disposed adjacent to and in thermal contact with the second surface 16 of the membrane 12. The plurality of micro-heating elements 28 each include a resistive thin Ti/Pt, Cr/Ni, Ti/W/Au, TaN, heavily-doped polysilicon_$p^{++}$ film or the like. Each of the plurality of micro-heating elements 28 has a thickness of between about 1 nm and about 1 μm and a length of between about 100 μm and about 1 cm. The resistivity of each of the plurality of micro-heating elements 28 is dependent primarily upon its geometry. Preferably, each of the twin-cell differential sensors 10 includes two micro-heating elements 28, corresponding to the first cell 24 and the second cell 26 defined by the frame 18, however other numbers may be used. Each of the plurality of micro-heating elements 28 is operable for receiving a current of between about 1 μA and about 50 mA and generating a temperature change of between about 0.1 degrees C. and about 500 degrees C. Each of the plurality of micro-heating elements 28 is heated at a rate of between about 1,000 degrees C./s and about 1,000,000 degrees C./s.

Figure 2:
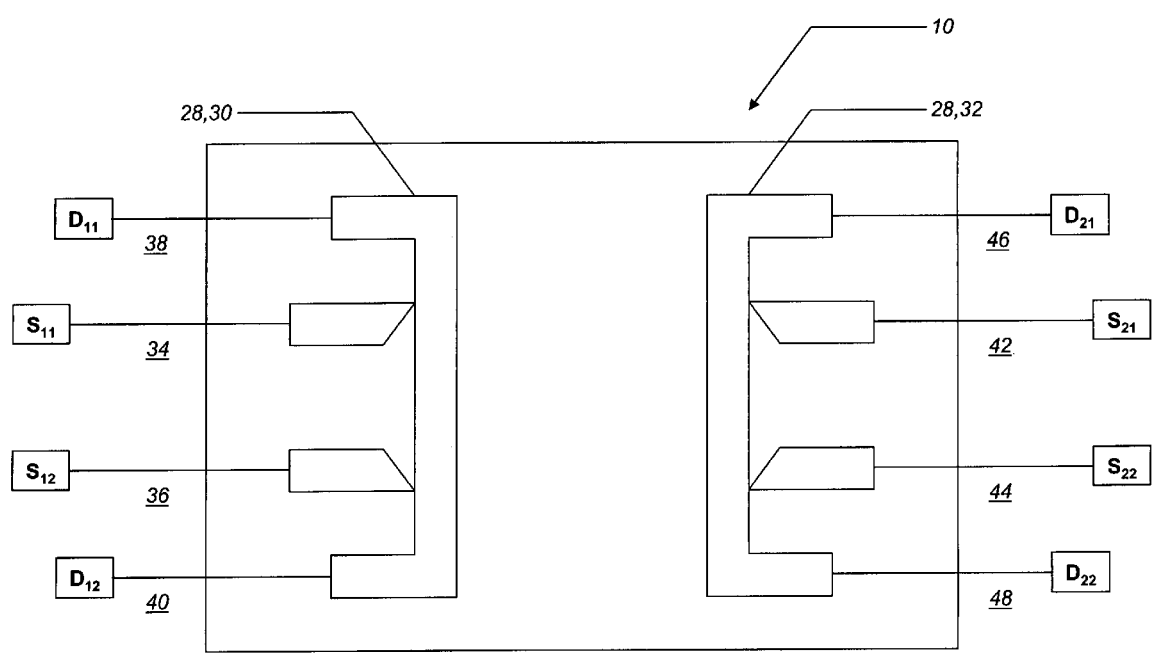
FIG. 2 is a planar top view of the twin-cell differential sensor of FIG. 1, highlighting a plurality of micro-heating elements associated with the twin-cell differential sensor.
Figure 3:
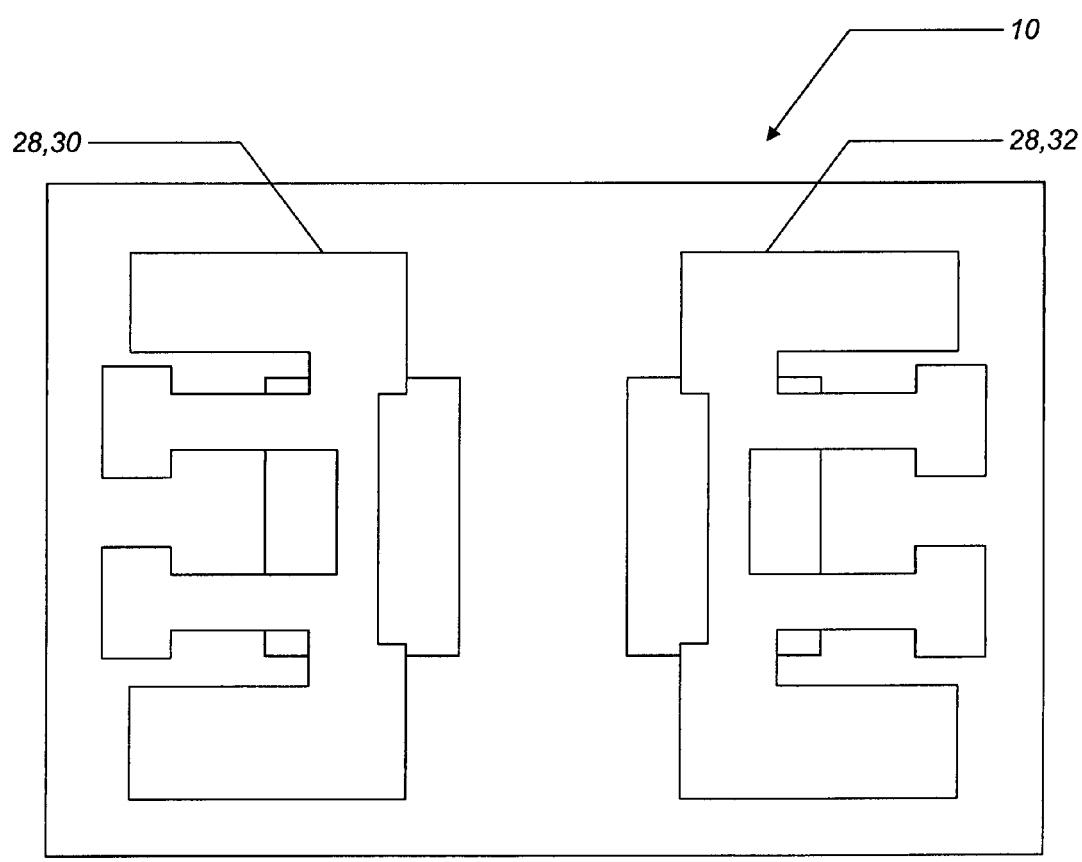
FIG. 3 is a planar top view of the twin-cell differential sensor of FIG. 1, highlighting a plurality of alternative micro-heating elements associated with the twin-cell differential sensor.

Referring to FIG. 2, each of the plurality of micro-heating elements 28 includes a plurality of contacts suitable for establishing a plurality of electrical connections. For the first micro-heating element 30, the plurality of electrical connections include a plurality of sourcemeter connections, $S_{11}$ 34 and $S_{12}$ 36, and a plurality of data acquisition connections, $D_{11}$ 38 and $D_{12}$ 40. For the second micro-heating element 32, the plurality of electrical connections include a plurality of sourcemeter connections, $S_{21}$ 42 and $S_{22}$ 44, and a plurality of data acquisition connections, $D_{21}$ 46 and $D_{22}$ 48. An alternative micro-heating element configuration is illustrated in FIG. 3. In general, each of the plurality of micro-heating elements 28 acts as a micro-heater and a resistive thermometer. Additional thermometers may be added to the nano-calorimeter device of the present invention in order to increase the sensitivity of the device. If additional thermometers are added, cross-talk between the micro-heater and the thermometers should be minimized by operating the additional thermometers at very small currents in order to minimize the heat generated by the additional thermometers.

Preferably, the one or more twin-cell differential sensors 10 (FIGS. 1, 2, and 3) are fabricated using one or more micro-electromechanical systems (MEMS) techniques, well known to those of ordinary skill in the art. For example, the starting material may include a double-sided polished Si wafer having a silicon nitride layer of well-controlled thickness disposed on each side. The fabrication process may include, first, forming the silicon nitride membranes and, second, forming the resistive thin Pt film micro-heating elements. Sub-micron heating elements may be patterned and fabricated using electron-beam lithography or the like. This fabrication process, as well as others, is described in greater detail herein below.

Figure 9:
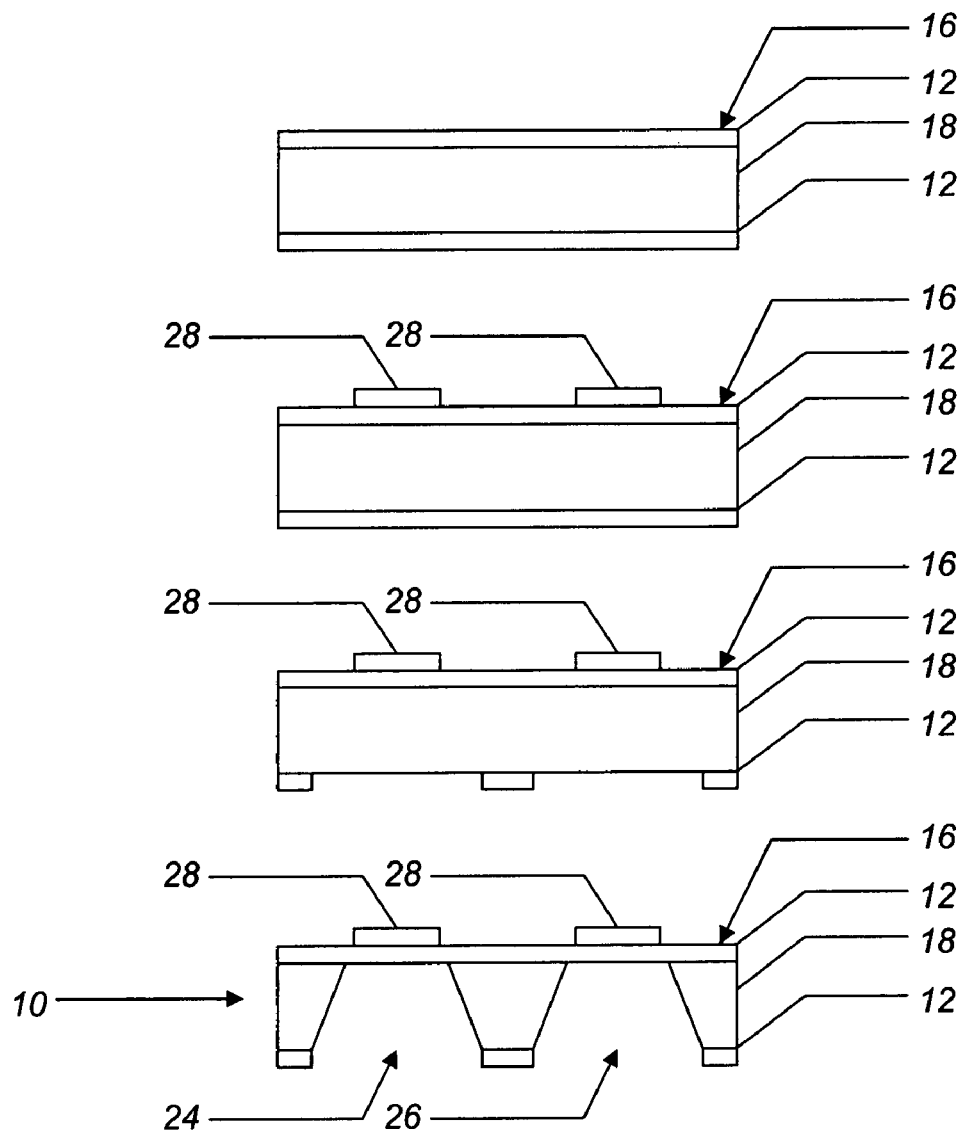
FIG. 9 is a series of cross-sectional side views illustrating the various steps involved in fabricating the twin-cell differential sensor of FIG. 1 (silicon frame)

For example, Referring to FIG. 9, in one embodiment, the one or more twin-cell differential sensors 10 may each be fabricated by depositing one or more thin (50 nm–150 nm) low-stress silicon nitride ($SiN_x$) layers 12 on one or more surfaces of a silicon layer 18. A plurality of Pt heater/thermometers 28 are then deposited on the exposed surface 16 of one of the silicon nitride layers 12 and the exposed surface of the other silicon nitride layer 12 is selectively etched in alignment with the plurality of Pt heater/thermometers 28. Finally, the silicon layer 18 is selectively etched to form the sample and reference cells 24,26 and the twin-cell differential sensor 10.

Figure 10:
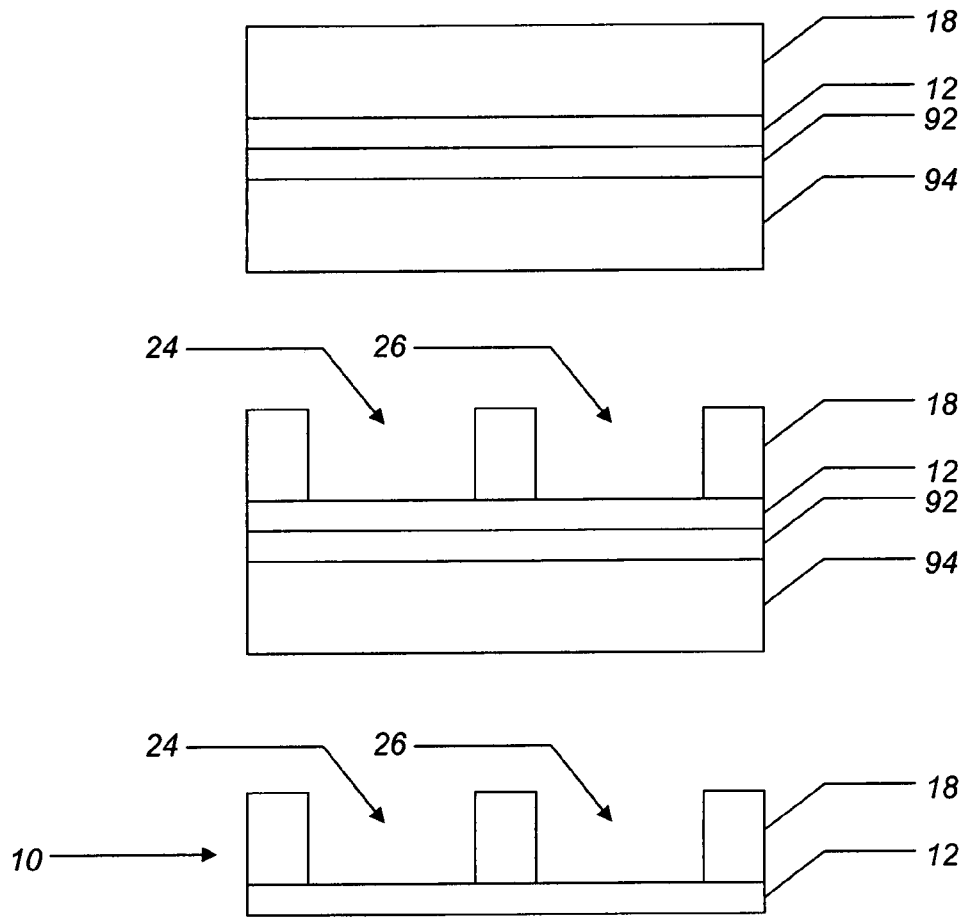
FIG. 10 is a series of cross-sectional side views illustrating the various steps involved in fabricating the twin-cell differential sensor of FIG. 1 (composite polymeric frame)

Referring to FIG. 10, in an alternative embodiment, the one or more twin-cell differential sensors 10 may each be fabricated by depositing a polymeric membrane 12 on a surface of a composite polymeric frame 18. A surface-functionalized silicon dioxide ($SiO_2$) layer 92 or the like is then deposited on the exposed surface of the polymeric membrane 12 and a PDMS slab 94 or the like is deposited on the exposed surface of the surface-functionalized silicon dioxide layer 92 or the like. Next, the composite polymeric frame 18 is embossed to form the sample and reference cells 24,26 of the twin-cell differential sensor 10. Finally, the structure is exposed to HF and the PDMS slab 94 or the like and the surface-functionalized silicon dioxide layer 92 or the like are removed to form the twin-cell differential sensor 10.

In a further embodiment, a polymeric nano-calorimeter device is fabricated by first forming a slab of silicone rubber on top of which successive layers of silicon dioxide ($SiO_2$) (with a thickness of between about 20 nm and about 100 nm), a self-assembled monolayer (SAM) (with a thickness of about 2 nm), a polymeric membrane (with a thickness of between about 20 nm and about 200 nm), and a composite polymeric/nano-particle film (with a thickness of between about 500 nm and about 600 $\mu$m) are deposited. The composite polymeric/nano-particle film is converted to form a polymeric frame that serves as a heat sink. Next, the silicon dioxide layer and the self-assembled monolayer are etched in order to separate the nano-calorimeter device (polymeric frame plus polymeric membrane) from the underlying slab of silicone rubber. Finally, the resistive thin Pt film micro-heating elements are deposited on the surface of the polymeric membrane. Again, sub-micron heating elements may be patterned and fabricated using electron-beam lithography or the like.

Figure 6:
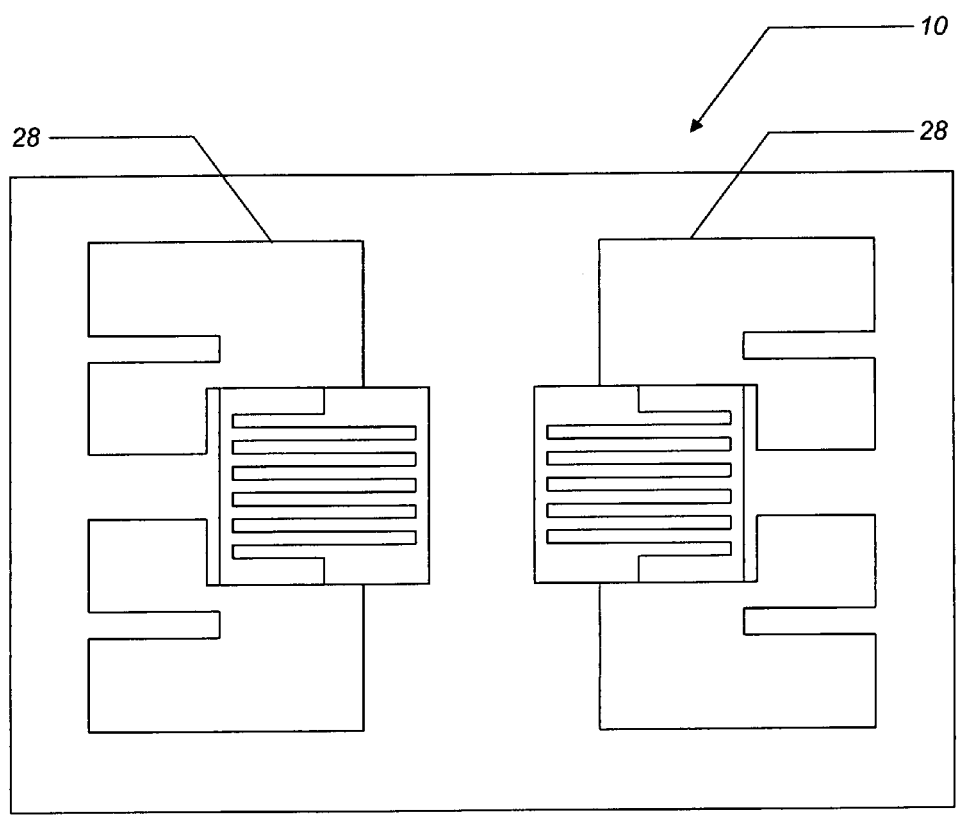
FIG. 6 is a planar top view of the twin-cell differential sensor of FIG. 1, highlighting a plurality of serpentine micro-heating elements associated with the twin-cell differential sensor.
Figure 7:
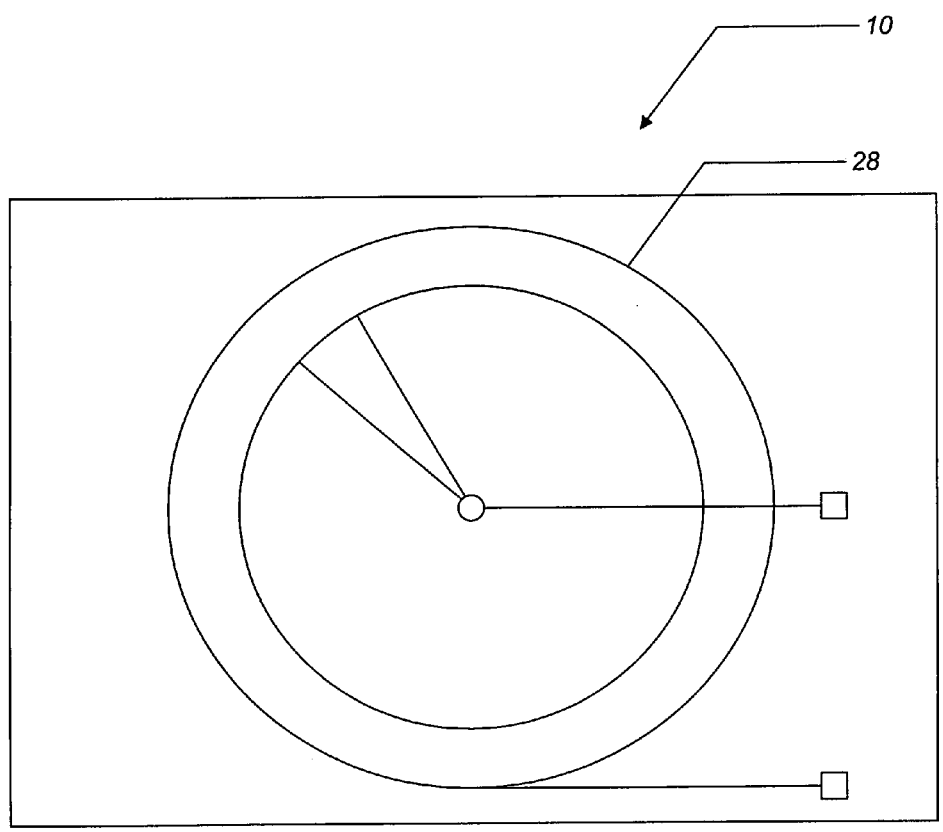
FIG. 7 is a planar top view of the twin-cell differential sensor of FIG. 1, highlighting one or more spiral micro-heating elements associated with the twin-cell differential sensor.

It will be readily apparent to those of ordinary skill in the art that variations in and modifications to the twin-cell differential sensors 10 described above are possible. The configuration of the frame 18 (FIG. 1) may be varied and/or modified, the configuration and position of the plurality of micro-heating elements 28 (FIGS. 1, 2, and 3) may be varied and/or modified, the configuration and position of the plurality of electrical connections may be varied and/or modified (including the number and type of electrical connections), etc. For example, serpentine (meandering) (see FIG. 6) or spiral (coiled) (see FIG. 7) micro-heating elements with a predetermined geometry, a predetermined number of turns, a predetermined pitch, and made of a predetermined material (Ni, Pt, TaN, etc.) may be used and may offer improved sensitivity to heat exchange across the membrane thickness. Therefore, such micro-heating elements mat be better suited than straight micro-heating elements for measuring and characterizing heat exchange from samples with relatively poor thermal conductivity, such as polymeric materials, for example. In designing such micro-heating elements, it is important to note the following considerations: an increased amount of metal on the membrane increases the addenda and decreases the resolution of the device; thinner micro-heating elements increase the resistance and improve the signal-to-noise ratio of the device; different metals have different thermal and chemical stabilities. Consequently, somewhere in the design space of the present invention there exists a set of parameters that produces optimal sensitivity, accuracy, resolution, stability, and overall performance for a given class of samples and type of measurements.

Figure 4:
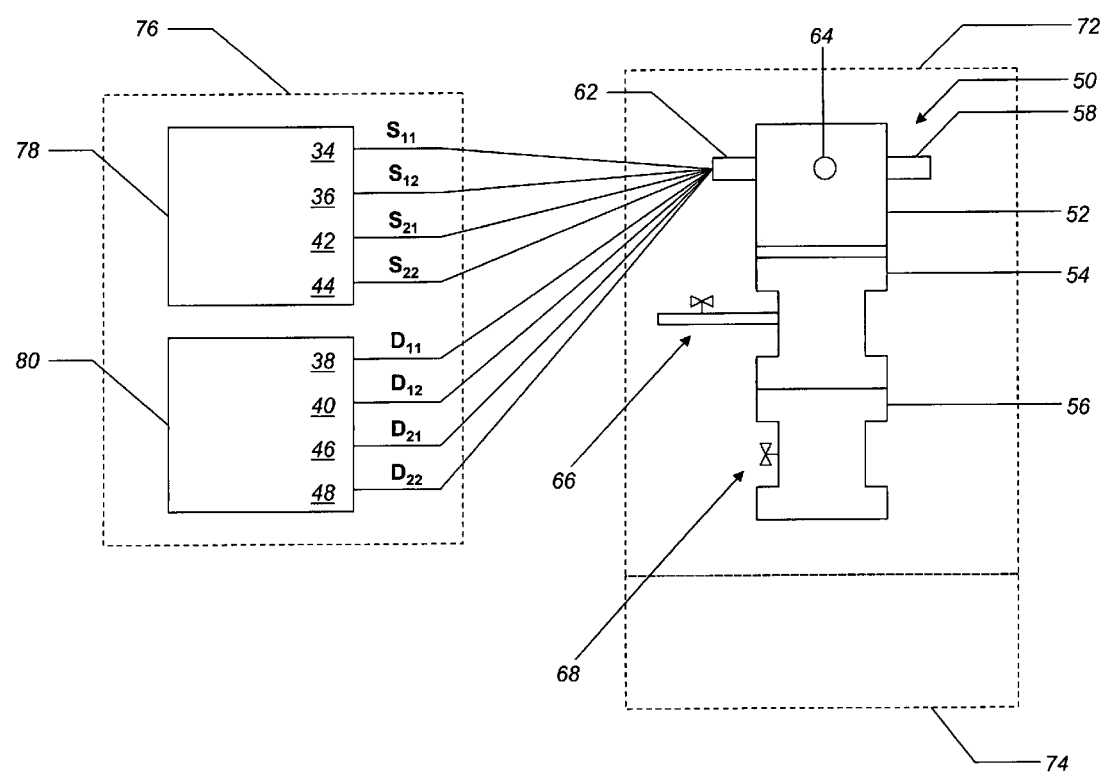
FIG. 4 is a schematic diagram illustrating one embodiment of a housing in which the twin-cell differential sensor of FIG. 1 is disposed, highlighting a vacuum chamber associated with the housing, a plurality of electrical connections associated with the plurality of micro-heating elements of FIGS. 2 and 3, and an electronic circuitry module associated with the nano-calorimeter device of the present invention.
Figure 5:
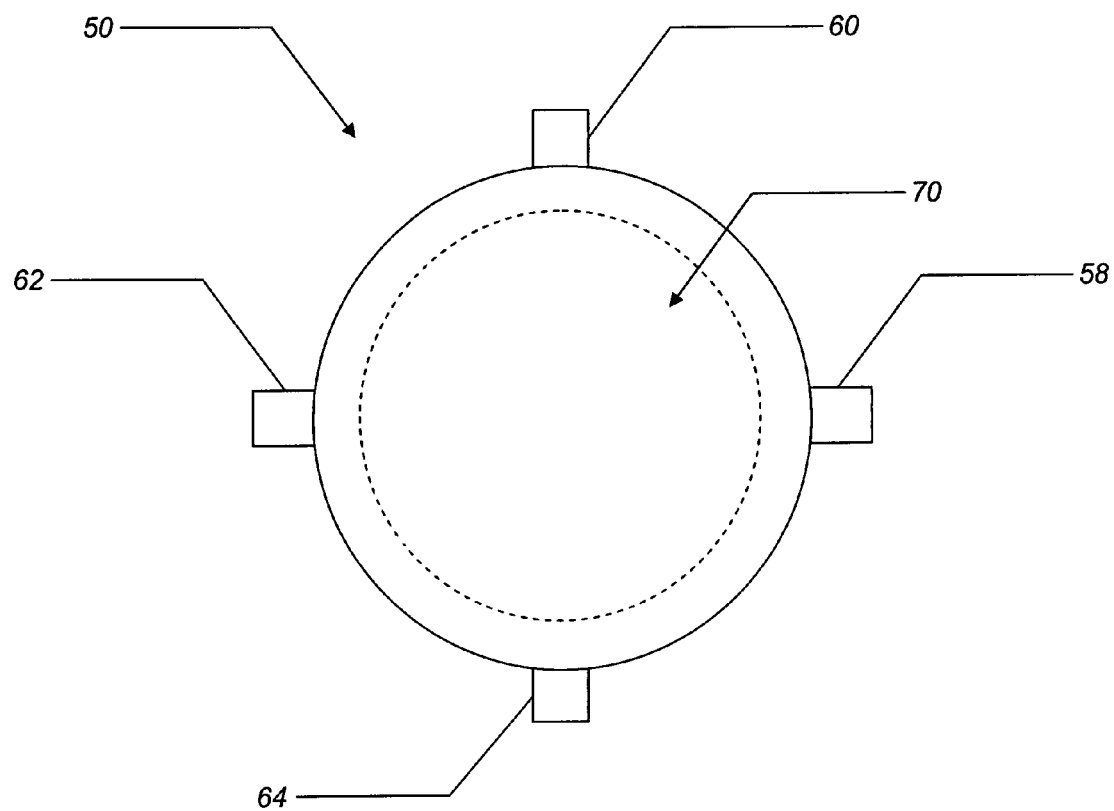
FIG. 5 is a planar end view of the housing of FIG. 4, highlighting a plurality of ports associated with the housing.

Referring to FIGS. 4 and 5, the one or more twin-cell differential sensors 10 (FIGS. 1, 2, and 3) are disposed within a housing 50 that includes a first section 52, a second section 54, and a third section 56. The first section 52 of the housing 50 includes a plurality of ports, including a first port 58 that provides a feed through for an ionization gauge (not shown), a second port 60 that provides a feed through for a venting purge, a third port 62 that provides a feed through for the plurality of electrical connections described above, and a fourth port 64 that provides a feed through for a plurality of temperature controllers (not shown), corresponding to each of the micro-heating elements 28 (FIGS. 1, 2, and 3) used. The second section 54 of the housing 50 includes a first valve 66 that acts as a vacuum inlet for a hot stage (described below) and the third section 56 of the housing 50 includes a second valve 68 that acts as a vacuum shut-off valve. Optionally, the end of the housing 50 includes a view port 70. Preferably, the housing 50 is disposed within a vacuum chamber 72 that is coupled to a vacuum pump 74, such as a 250 V vacuum pump or the like. The vacuum pump 74 is operable for creating a vacuum of about $10^{-7}$ Torr in the vacuum chamber 72.

The plurality of micro-heating elements 28 are coupled to an electronic circuitry module 76 that includes a sourcemeter 78 and a data acquisition system 80. As described above, the sourcemeter 78 includes a plurality of sourcemeter connections, $S_{11}$ 34, $S_{12}$ 36, $S_{21}$ 42, and $S_{22}$ 44, and the data acquisition system 80 includes a plurality of data acquisition connections, $D_{11}$ 38, $D_{12}$ 40, $D_{21}$ 46, and $D_{22}$ 48. In general, the sourcemeter 78 comprises an analogue output current card operable for generating the current necessary to heat the plurality of micro-heating elements 28. Likewise, the data acquisition system 80 comprises an analogue input card (DAQ) and appropriate software operable for acquiring and analyzing data regarding, for example, the power associated with each of the plurality of micro-heating elements 28, the temperature associated with each of the plurality of micro-heating elements 28, the heat capacity associated with each of the plurality of samples, etc. Any commercially-available or customized hardware and software that meet the required powers, temperatures, currents, and cycle times are acceptable.

Figure 11:
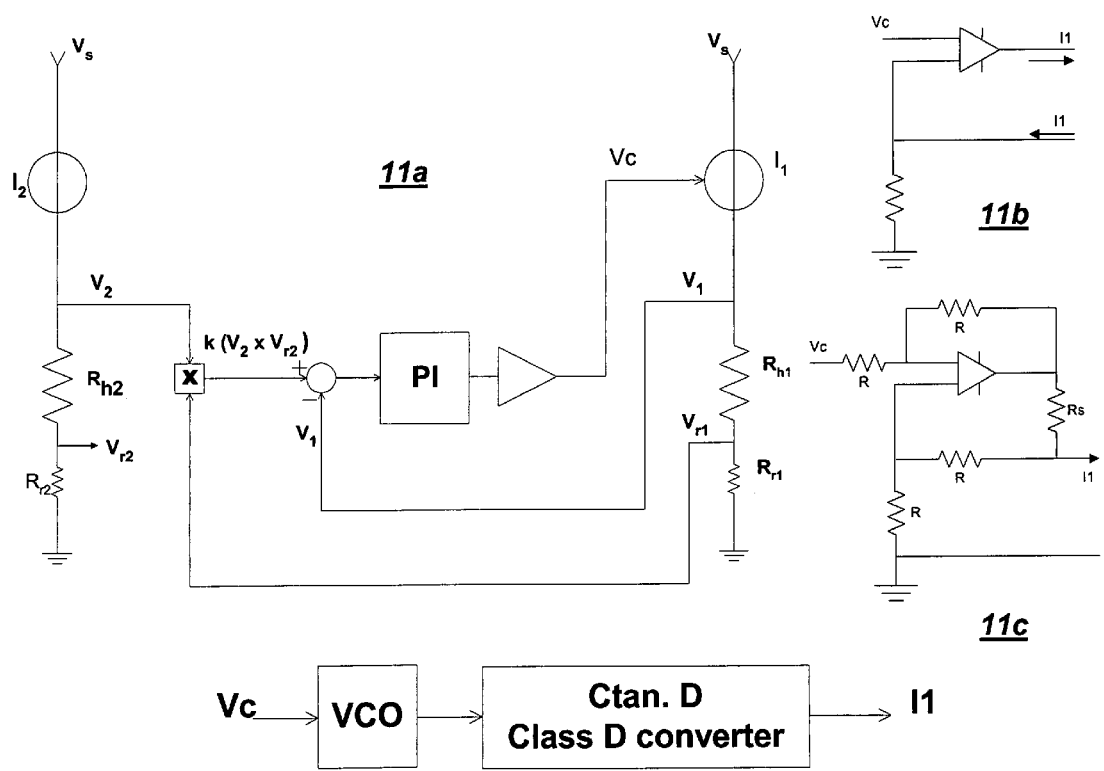
FIG. 11 is a circuit diagram illustrating the power-compensation scheme of the nano-calorimeter device of the present invention.

FIG. 11 is a circuit diagram illustrating the power-compensation scheme of the nano-calorimeter device of the present invention. The nano-calorimeter device may be operated in a power-compensation mode in conjunction with a probing and analytical method such as optical beam probing at a predetermined wavelength and a spectroscopic method, electron beam probing and an x-ray spectroscopic method, magnetic probing, a photoaccoustic method, a gravimetric method, or a vibration-based method. Temperature compensation is calculated using equations 1–4, with $I_2$ being a constant current source and $I_1$ being a controlled current source:

$$V_1 = I_1 \cdot R_1(T) + I_1 \cdot R_r = I_1 \cdot (R_1(T) + R_r), \quad (1)$$

$$V_2 = I_2 \cdot R_2(T) + I_2 \cdot R_r = I_2 \cdot (R_2(T) + R_r), \quad (2)$$

$$R_1(T) = R_2(T) = [(V_2 - I_2 \cdot R_r)/I_2] = (V_2/I_2) - R_r, \text{ and} \quad (3)$$

$$V_1 = [(R_r \cdot I_1)/(R_r \cdot I_2)] \cdot V_2 = K \cdot V_r \cdot V_2, \text{ where } K = R_r \cdot I_2. \quad (4)$$

FIGS. 11a, 11b, and 11c illustrate three possible implementations of the current source 11 controlled by voltage $V_c$.

In general, the nano-calorimeter device of the present invention is used to measure and characterize heat capacities, thermal transitions (such as melting points and glass transition temperatures), thermal changes associated with the formation of new products (such as heats of reaction in single and multi-layer samples), and the like. The following may be measured and characterized: piezoelectric effect, thermoelectric effect, adhesion strength, crystallization phenomena in thin films, most of the thermodynamic entities in confined thin films, magnetic transition temperatures, stress-related phase transitions, light-exposure related phase transitions, etc. Advantageously, the nano-calorimeter device of the present invention allows for differential scanning measurements and, in a symmetrical configuration, inherent measurement errors due to thermal leakage are equal in both cells. Thus, these inherent measurement errors may be counterbalanced. Because the one or more twin-cell differential sensors 10 are disposed in the vacuum chamber 72, thermal leakage due to convection is minimized. Solid state cooling of the frame 18 (FIG. 1) minimizes thermal leakage by conduction. Because the one or more twin-cell differential sensors 10 are shielded, thermal leakage due to radiation is minimized.

The nano-calorimeter device of the present invention may be combined with additional integrated or external parts in order to study phenomena of interest that produce relatively small changes in thermodynamic and other physical properties in materials confined to essentially nano-scale dimensions. For example, a nano-magneto-calorimeter may be formed by combining the nano-calorimeter device of the present invention with a time-varying external magnetic field. The piezoelectric effect may be studied by integrating cantilever microstructures with the elements described above.

Although the present invention has been illustrated and described with reference to preferred embodiments and examples thereof, it will be readily apparent to those of ordinary skill in the art that other embodiments and examples may perform similar functions and/or achieve similar results. All such equivalent embodiments and examples are within the spirit and scope of the present invention and are intended to be covered by the following claims.

What is claimed is:

1. A nano-calorimeter device operable for measuring and characterizing the thermodynamic and other physical properties of materials that are confined to essentially nano-scale dimensions, the nano-calorimeter device comprising:
   a thin film membrane having a first surface and a second surface;
   a frame structure disposed adjacent to and in thermal contact with the first surface of the thin film membrane, the frame structure defining a plurality of hollow cells adjacent to and in thermal contact with the first surface of the thin film membrane;
   a thermally-insulating dielectric layer disposed between the first surface of the thin film membrane and the frame structure, wherein the thermally-insulating dielectric layer is adjacent to and in thermal contact with all or a portion of the first surface of the thin film membrane; and
   one or more micro-heating elements disposed adjacent to and in thermal contact with the second surface of the thin film membrane, the location of the one or more micro-heating elements disposed adjacent to the second surface of the thin film membrane substantially corresponding to the location of the plurality of hollow cells defined adjacent to the first surface of the thin film membrane.

2. The nano-calorimeter device of claim 1, wherein the thin film membrane comprises a material selected from the group consisting of SiNx, Si3Nx, and a polymeric material.

3. The nano-calorimeter device of claim 1, wherein the thin film membrane has a thickness of between about 20 nm and about 5000 nm.

4. The nano-calorimeter device of claim 1, wherein the frame structure comprises a material selected from the group consisting of Si, SiC, a composite polymeric material, a composite polymeric material comprising dispersed thermally-conductive nano-particles, and a metallic material.

5. The nano-calorimeter device of claim 1, wherein the frame structure has a thickness of between about 50 $\mu$m and about 600 $\mu$m.

6. The nano-calorimeter device of claim 1, wherein the one or more micro-heating elements comprise one or more micro-heater/thermometer devices.

7. The nano-calorimeter device of claim 1, wherein the one or more micro-heating elements comprise one or more devices selected from the group consisting of one or more substantially-straight micro-heater/thermometer devices, one or more serpentine micro-heater/thermometer devices, and one or more spiral micro-heater/thermometer devices.

8. The nano-calorimeter device of claim 1, wherein the one or more micro-heating elements each comprise a material selected from the group consisting of Pt, Ni, Au, Ti/Pt, Cr/Ni, Ti/W/Au, TaN, and heavily-doped polysilicon_p++.

9. The nano-calorimeter device of claim 1, wherein the one or more micro-heating elements each have a thickness of between about 1 nm and about 1 $\mu$m.

10. The nano-calorimeter device of claim 1, wherein each of the one or more micro-heating elements is operable for receiving a current of between about 1 $\mu$A and about 50 mA.

11. The nano-calorimeter device of claim 1, wherein each of the one or more micro-heating elements is operable for generating a temperature change of between about 0.1 degrees C. and about 500 degrees C.

12. The nano-calorimeter device of claim 1, wherein each of the one or more micro-heating elements is heated at a rate of between about 1,000 degrees C./s and about 1,000,000 degrees C./s.

13. The nano-calorimeter device of claim 1, further comprising a nano-scale sample disposed adjacent to one of the first surface and the second surface of the thin film membrane, the location of the nano-scale sample disposed adjacent to one of the first surface and the second surface of the thin film membrane substantially corresponding to the location of the plurality of hollow cells defined adjacent to the first surface of the thin film membrane and the location of the one or more micro-heating elements disposed adjacent to the second surface of the thin film membrane.

14. The nano-calorimeter device of claim 13, wherein the nano-scale sample comprises a material selected from the group consisting of a polymeric material, a ceramic material, a metallic material, a composite material, a biomaterial, a liquid, and an adsorbed gas.

15. The nano-calorimeter device of claim 13, wherein the nano-scale sample has a thickness of between about 1 pm and about 10 microns.

16. The nano-calorimeter device of claim 13, wherein the nano-scale sample has a mass of between about 1 ng and about 1000 $\mu$g.

17. The nano-calorimeter device of claim 1, wherein the nano-calorimeter device is operated in a power-compensation mode.

18. A method for fabricating and using a nano-calorimeter device operable for measuring and characterizing the thermodynamic and other physical properties of materials that are confined to essentially nano-scale dimensions, the method comprising:
    providing a thin film membrane having a first surface and a second surface;
    disposing a frame structure adjacent to and in thermal contact with the first surface of the thin film membrane, the frame structure defining a plurality of hollow cells adjacent to and in thermal contact with the first surface of the thin film membrane;
    disposing a thermally-insulating dielectric layer adjacent to and in thermal contact with all or a portion of the first surface of the thin film membrane and between the first surface of the thin film membrane and the frame structure; and
    disposing one or more micro-heating elements adjacent to and in thermal contact with the second surface of the thin film membrane, the location of the one or more micro-heating elements disposed adjacent to the second surface of the thin film membrane substantially corresponding to the location of the plurality of hollow cells defined adjacent to the first surface of the thin film membrane.

19. The method of claim 18, wherein the thin film membrane comprises a material selected from the group consisting of SiNx, Si3Nx, and a polymeric material.

20. The method of claim 18, wherein the thin film membrane has a thickness of between about 20 nm and about 5000 nm.

21. The method of claim 18, wherein the frame structure comprises a material selected from the group consisting of Si, SiC, a composite polymeric material, a composite polymeric material comprising dispersed thermally-conductive nano-particles, and a metallic material.

22. The method of claim 18, wherein the frame structure has a thickness of between about 50 $\mu$m and about 600 $\mu$m.

23. The method of claim 18, wherein the one or more micro-heating elements comprise one or more micro-heater/thermometer devices.

24. The method of claim 18, wherein the one or more micro-heating elements comprise one or more devices selected from the group consisting of one or more substantially-straight micro-heater/thermometer devices, one or more serpentine micro-heater/thermometer devices, and one or more spiral micro-heater/thermometer devices.

25. The method of claim 18, wherein the one or more micro-heating elements each comprise a material selected from the group consisting of Pt, Ni, Au, Ti/Pt, Cr/Ni, Ti/W/Au, TaN, and heavily-doped polysilicon_p++.

26. The method of claim 18, wherein the one or more micro-heating elements each have a thickness of between about 1 nm and about 1 $\mu$m.

27. The method of claim 18, further comprising providing each of the one or more micro-heating elements with a current of between about 1 $\mu$A and about 50 mA.

28. The method of claim 18, further comprising generating a temperature change of between about 0.1 degrees C. and about 500 degrees C. in each of the one or more micro-heating elements.

29. The method of claim 18, further comprising heating each of the one or more micro-heating elements at a rate of between about 1,000 degrees C./s and about 1,000,000 degrees C./s.

30. The method of claim 18, further comprising disposing a nano-scale sample adjacent to one of the first surface and the second surface of the thin film membrane, the location of the nano-scale sample disposed adjacent to one of the first surface and the second surface of the thin film membrane substantially corresponding to the location of the plurality of hollow cells defined adjacent to the first surface of the thin film membrane and the location of the one or more micro-heating elements disposed adjacent to the second surface of the thin film membrane.

31. The method of claim 30, wherein the nano-scale sample comprises a material selected from the group consisting of a polymeric material, a ceramic material, a metallic material, a composite material, a biomaterial, a liquid, and an adsorbed gas.

32. The method of claim 30, wherein the nano-scale sample has a thickness of between about 1 pm and about 10 microns.

33. The method of claim 30, wherein the nano-scale sample has a mass of between about 1 ng and about 1000 $\mu$g.

34. The method of claim 18, further comprising operating the nano-calorimeter device in a power-compensation mode.

35. The method of claim 34, further comprising operating the nano-calorimeter device in a power-compensation mode in conjunction with a probing and analytical method selected from the group consisting of optical beam probing at a predetermined wavelength and a spectroscopic method, electron beam probing and an x-ray spectroscopic method, magnetic probing, a photoaccoustic method, a gravimetric method, and a vibration-based method.

* * * * *